United States Patent
Ebetino et al.

(10) Patent No.: US 7,781,418 B2
(45) Date of Patent: Aug. 24, 2010

(54) COMPOSITION FOR TREATING BONE DISORDERS

(75) Inventors: Frank Hallock Ebetino, Cincinnati, OH (US); Robert Kenneth Boeckman, Jr., Honeoye Falls, NY (US); Xinyi Song, Rochester, NY (US)

(73) Assignee: Isis Innovation Ltd., Summertown, Oxford (GB)

( * ) Notice: Subject to any disclaimer, the term of this patent is extended or adjusted under 35 U.S.C. 154(b) by 176 days.

(21) Appl. No.: 12/001,318

(22) Filed: Dec. 11, 2007

(65) Prior Publication Data

US 2009/0069272 A1 Mar. 12, 2009

Related U.S. Application Data

(60) Provisional application No. 60/874,821, filed on Dec. 14, 2006.

(51) Int. Cl.
- *A61K 31/675* (2006.01)
- *A61K 31/44* (2006.01)
- *A01N 43/42* (2006.01)

(52) U.S. Cl. .......................... 514/80; 514/299

(58) Field of Classification Search ................ 514/80, 514/299
See application file for complete search history.

(56) References Cited

U.S. PATENT DOCUMENTS 4,868,164 A   9/1989   Ebetino et al.

OTHER PUBLICATIONS

Szabo et al., J. med. Chem., 2002, vol. 45, pp. 2894-2903.*

Dunford, J.E. et al., ,,Structure-activity Relationships For Inhibition Of Farnesyl Diphosphate Synthyase In Vitro and Inhibition Of Bone Resorption In Vivo By Nitrogen-Containing Bisphosphonates, Journal of Pharmacology and Experimental Therapeutics, vol. 296, No. 2, Feb. 2001, pp. 235-242.

Ebetino, F.H. et al., "Bisphosphonates: Molecular Modeling, Structure-activity Relationships and The Rational Design Of New Analogs," Phosphorus, Sulfur and Silicon, vol. 76, No. 1-4, 1993, pp. 151-154.

Ebetino, F.H. et al., "Studies on a Potent New Antiresorptive Bisphosphonate Class, Cis-Octahydro-1-Pyridine-6,6-Bisphosphonic Acid, NE-58025 and Its Analogues," Osteoporosis, vol. 3, 1980, pp. 1344-1346.

Luckman, S.P. et al., "Heterocycle-containing Bisphosphonates Cause Apoptosis and Inhibit Bone Resorption By Preventing Protein Prenylation: Evidence From Structure-activity Relationships in J774 Macrophages," Journal Of Bone And Mineral Research, vol. 13, No. 11 1998, pp. 1668-1678.

Rogers, M.J. et al., "Structure-activity Relationships of New Heterocycle-Containing Bisphosphonates As Inhibitors Of Bone Resorption and As Inhibitors Of Growth of Dictyosteliurn Discoideum Amoebae," Molecular Pharmacology, vol. 47, No. 2, Feb. 1995, pp. 398-402.

Szabo, C.M. et al., "An Investigation of Bone Resorption and Dictyostelium Discoideum Growth Inhibition By Bisphosphonate Drugs," Journal of Medicinal Chemistry, vol. 45, No. 14, Jul. 4, 2002, pp. 2894-2903.

* cited by examiner

*Primary Examiner*—D. Margaret Seaman
*Assistant Examiner*—Niloofar Rahmani
(74) *Attorney, Agent, or Firm*—Thomas, Kayden, Horstemeyer & Risley, LLP; Todd Deveau

(57) ABSTRACT

Disclosed is a new composition of matter, substantially enantiomerically pure (1R,6S)-2-Azabicyclo-[4.3.0]nonane-8,8-diphosphonic acid, methods of preparing this new composition of matter, a pharmaceutical composition comprising the new composition, and administration of the composition in methods of treating bone disorders such as osteoporosis, osteolytic bone metastasis, rheumatoid arthritis and osteoarthritis.

6 Claims, No Drawings

COMPOSITION FOR TREATING BONE DISORDERS

CROSS-REFERENCE TO RELATED APPLICATION

This claims priority to U.S. Provisional Application Ser. No. 60/874,821, filed Dec. 14, 2006.

TECHNICAL FIELD

The present invention is directed to a new composition of matter, a method of making the new composition of matter, a pharmaceutical composition comprising the new composition, and administration of the composition in methods of treating bone disorders such as osteoporosis, Paget's Disease (osteitis deformans), hyperparathyroidism, hypercalcemia of malignancy, osteolytic bone metastasis, myositis ossificans progressiva, calcinosis universalis, arthritis, neuritis, bursitis, and tendonitis.

BACKGROUND OF THE INVENTION

The present invention relates to a novel compound and further relates to pharmaceutical compositions which contain the novel compound of the present invention. The present invention also related to a method of preparing the novel compound of the present invention. Finally, the present invention relates to a method for treating or preventing conditions characterized by abnormal calcium and phosphate metabolism by utilizing a compound or pharmaceutical composition of the present invention.

A number of pathological conditions which can afflict humans and lower animals involve abnormal calcium and phosphate metabolism. Such conditions may be divided into two broad categories:

(1) Conditions which are characterized by anomalous mobilization of calcium and phosphate leading to general or specific bone loss, or excessively high calcium and phosphate levels in the fluids of the body, such as osteoporosis, osteolytic bone metastasis, and Paget's Disease. Such conditions are sometimes referred to herein as pathological hard tissue demineralizations.

(2) Conditions which cause or result from deposition of calcium and phosphate anomalously in the body, such as arthritis. These conditions are sometimes referred to herein as pathological calcifications.

A variety of polyphosphonic acid derivatives have been proposed for use in the treatment and prophylaxis of conditions involving abnormal calcium and phosphate metabolism. For example, U.S. Pat. No. 3,683,080 discloses compositions containing polyphosphonates, in particular diphosphonates, and their use in inhibiting anomolous deposition and mobilization of calcium phosphate in animal tissue; U.S. Pat. No. 4,230,700 discloses composition containing certain phosphonate compounds (e.g., cycloalkyl-substituted hydroxyethane diphosphonates) in combination with vitamin D-like compounds useful in inhibiting mobilization of calcium phosphate in animal tissue; U.S. Pat. No. 3,988,443 discloses azacycloalkane-2,2-diphosphonate compound said to be useful as sequestering agents and as agents in the treatment of conditions related to the abnormal deposition or dissolution of difficulty soluble calcium salts in the animal body; and European Patent Publication No. 189,662 which discloses various specific cyclic diphosphonate compounds said to be useful as sequestering agents or as agents in the treatment of conditions characterized by abnormal calcium and phosphate metabolism. The disclosures of all these patents and applications are incorporated herein by reference in their entirety.

In spite of this and much other research into the use of diphosphonates to treat bone-metabolism conditions, there continues to be a need for new bone-active agents. The object of the present invention is therefore to provide new bone-active diphosphonate compounds having relatively high potency for inhibiting bone re-sorption. Furthermore, an object of the present invention is to provide new bone-active diphosphonate compounds with low toxicity and favorable therapeutic indices. It is a further object of the present invention to provide pharmaceutical compositions useful for the treatment and prophylaxis of abnormal calcium and phosphate metabolism. In addition, it is an object of the present invention to provide methods for treating or preventing conditions characterized by abnormal calcium and phosphate metabolism in humans or lower animals.

U.S. Pat. No. 4,868,164 discloses compounds having nitrogen-containing, saturated bicyclic cyclopentane-fused rings which are germinally disubstituted with phosphonate groups. Preferred are substituted or unsubstituted octahydro pyrindine diphosphonate compounds, especially substituted or unsubstituted octahydro 1-pyrindine-6,6-diphosphonic acid compounds, and the pharmaceutically-acceptable salts and esters thereof. The '164 patent further discloses pharmaceutical compositions containing a safe and effective amount of said compounds, and a pharmaceutically-acceptable carrier.

The racemic mixture of the 1R,6S and 1S,6R isomers is the subject of U.S. Pat. No. 4,868,164. The '164 patent describes the racemic mixture and specifically the cis-ring juncture of the other enantiomer, (1S,6R). The racemic mixture and the 1S,6R enantiomer were also described in a paper published in 1990. (Ebetino et al., "Studies on a Potent New Antiresorptive Bisphosphonate Class: Cis- Octahydro-1-pyrindine-6,6-Bisphosphonic Acid, Ne-58025 and its Analogues" In: Osteoporosis 1990, 3, 3rd International Symposium on Osteoporosis, Copenhagen, Denmark, Oct. 14-20, 1990, edited by C. Christiansen and K. Overgaard, Handelstrykkeriet Aalborg Aps, Aalborg, Denmark, 1990, p. 1344-1346).

Farnesyl pyrophosphate synthase (FPPS) is a key regulatory enzyme in the mevalonate pathway. This pathway, ubiquitous in mammalian cells, provides essential lipid molecules, such as cholesterol and isoprenoids, with the latter necessary for posttranslational prenylation of small GTPases. The blockade of this pathway is a concept that has found widespread clinical use, with statins as drugs that inhibit hydroxymethylglutaryl-CoA reductase and reduce cholesterol biosynthesis, and nitrogen-containing bisphosphonates (N-BPs) as drugs for osteoporosis therapy that target FPPS and inhibit protein prenylation. In the case of N-BPs, the unique bone-targeting pharmacokinetic properties of these compounds cause selective inhibition of FPPS and loss of prenylated proteins in osteoclasts, thereby inhibiting the bone-destroying function of these cells.

The inventors herein find that a specific isomer, (1R,6S)-2-Azabicyclo-[4.3.0]nonane-8,8-diphosphonic acid, shows at least an order of magnitude more activity (for example, $IC_{50}=15$ nM) than its 1S,6R enantiomer, (for example, $IC_{50}=359$ nM), in the farnesyl pyrophosphate synthase (FPPS) inhibition assay.

BRIEF SUMMARY OF THE INVENTION

The present invention is directed to a new composition of matter, substantially enantiomerically pure (1R,6S)-2-Azabicyclo-[4.3.0]nonane-8,8-diphosphonic acid, a pharmaceutical composition comprising the new composition, and administration of the composition in methods of treating bone disorders such as Paget's Disease and osteoporosis.

In one aspect of the present invention, there is a composition of matter consisting of substantially enantiomerically pure (1R,6S)-2-Azabicyclo-[4.3.0]nonane-8,8-diphosphonic acid.

In another aspect of the present invention, there is a pharmaceutical composition comprising substantially enantiomerically pure (1R,6S)-2-Azabicyclo-[4.3.0]nonane-8,8-diphosphonic acid. In some embodiments, the pharmaceutical composition comprises a solid oral dosage form. In the same or additional embodiments, the solid oral dosage form is a tablet.

In another aspect of the present invention, there is a method of treating or preventing a condition of bone metabolism, said method comprising the step of administering to a patient suffering from or at risk for said condition of bone metabolism a pharmaceutical composition comprising substantially enantiomerically pure (1R,6S)-2-Azabicyclo-[4.3.0]nonane-8,8-diphosphonic acid. In some embodiments, the step of administering a pharmaceutical composition comprises administering a solid oral dosage form comprising said pharmaceutical composition. In preferred embodiments, the solid oral dosage form is a tablet. In some embodiments, the condition of bone metabolism is osteoporosis. In some embodiments, the condition of bone metabolism is Paget's Disease.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

As used herein, "a" or "an" means one or more. Unless otherwise indicated, the singular contains the plural and the plural contains the singular.

As used herein, the term "2-Azabicyclo-[4.3.0]nonane-8,8-diphosphonic acid" refers to the free phosphonic acid forms of the compound, or any salt of one or both of the phosphonate groups (or any mixed salt). Additionally, this includes any and all salts of the amino group of the compound.

As used herein, "substantially enantiomerically pure" means a purity of at least 95% of a referenced enantiomer and at most 5% of the other enantiomer. In another embodiment "substantially enantiomerically pure" means a purity of at least 98% of a reference enantiomer and at most 2% of the other enantiomer.

The (1R,6S)-isomer of 2-Azabicyclo-[4.3.0]nonane-8,8-diphosphonic acid, shows at least an order of magnitude more activity (for example, $IC_{50}=15$ nM) than its enantiomer, (1S,6R) (for example, $IC_{50}=359$ nM), in the farnesyl pyrophosphate synthase (FPPS) inhibition assay. The activity of the racemic mixture, is approximately 42 nM. The relevant structures are:

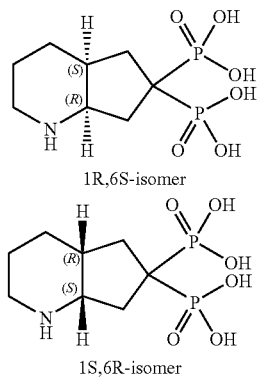

1R,6S-isomer 1S,6R-isomer

The increased activity of the (1R, 6S)-isomer may be seen by comparing the lowest effective dose of each compound and the racemic mixture, as exemplified by one finding as follows:

| | Lowest Effective Dose (mg P/kg)[1] | |
|---|---|---|
| Compound | Bone Mineral Content (BMC) | Bone Mineral Density (BMD) |
| Racemic Mixture | 0.03 | 0.03 |
| 1R,6S Isomer | 0.01 | 0.01 |
| 1S,6R Isomer | >0.1[2] | 0.1 |

[1]Data from head-to-head comparison of all three compounds.
[2]Highest dose tested.

Polyphosphonates are evaluated for in vivo bone resorption inhibition and mineralization inhibition in an animal model system known in the field of bone metabolism as the Schenk Model. Further, data shows that the (1R,6S)-isomer is more active in the Schenk assay than either its enantiomer (1S,6R) or the corresponding racemic mixture. The Schenk assay is an evaluation of in vivo bone resorption and mineralization in an animal model system known in the field of bone metabolism research. The general principles of this model system are disclosed in Shinoda, et. al., Calicif. Tissue Int., 35, 87-99 (1983); and in Schenk, et. al., Calcif. Tissue Res., 11, 196-214 (1973), the disclosures of which are incorporated herein by reference. The Schenk model is well known in the field and has been described in various documents including: U.S. Pat. No. 5,583,122 and U.S. Pat. No. 4,761,406.

Substantially enantiomerically pure (1R,6S)-2-Azabicyclo-[4.3.0]nonane-8,8-diphosphonic acid can be prepared by chiral separation of the racemic mixture of the 1R,6S and 1S,6R isomers prepared for example as described in U.S. Pat. No. 4,868,164. For example, separation by chromatography on a chiral column or resolution by crystallization of chiral salts are described in the literature. Another method to prepare substantially enantiomerically pure (1R,6S)-2-Azabicyclo-[4.3.0]nonane-8,8-diphosphonic acid is stereoselective synthesis of the two enantiomers is now described. A synthesis of the 1R,6S isomer is provided below.

Synthesis of 1R,6S Isomer

The present invention is further directed to a method of preparing a substantially enantiomerically pure (1R,6S)-2-Azabicyclo-[4.3.0]nonane-8,8-diphosphonic acid compound comprising:
a. conversion of Compound 6 to form Compound 7,
b. conversion of Compound 7 to form Compound 8,
c. conversion of Compound 8 to form Compound 9,
d. conversion of Compound 9 to form Compound 10, and
e. conversion of Compound 10 to form said compound.

Compound 6, Compound 7, Compound 8, and Compound 9 as referenced herein, including the appended claims, are each structurally depicted in "Scheme for the synthesis of Compound 1, 2, and 3", below.

The following are non-limiting methods to convert: Compound 6 to Compound 7; Compound 7 to Compound 8; Compound 8 to Compound 9; Compound 9 to Compound 10; and Compound 10 to the inventive compound herein. The ordinarily skilled artisan will understand that the structures of Compounds 6, 7, 8, 9, and 10 may be modified, for example, through use of varying reagents and the like, and are intended to include all foreseeable structures known to the ordinarily skilled artisan. In addition, independently, each of Compounds 6, 7, 8, 9, and 10 may be formed and isolated to a desired level of purity; alternatively, and independently, each of Compounds 6, 7, 8, 9, and 10, may be formed in situ without isolation or purification. The ordinarily skilled artisan will readily make such choices given the benefit of this specification.

For example, from Compound 6, the first step is reduction of Compound 6, for example with a reducing agent, to form Compound 7. Reducing agents may include hydrides and are commonly used in organic synthesis to reduce functional groups such as esters, carboxylic acids, ketones and aldehydes to the corresponding alcohols. Non-limiting examples of hydride reducing agents include: lithium aluminum hydride, sodium borohydride, sodium bis(2-methoxyethoxy) aluminum hydride, and the like. Lithium aluminum hydride is illustrated in the synthetic example set forth below.

Next, Compound 7 is deprotected to form Compound 8. Deprotection is the process of removing protecting groups during the synthesis of complex organic molecules. A number of deprotection methods are commonly known; hydrogenation is exemplified below.

Compound 8 is then converted to Compound 9, i.e., "protecting" the alcohols. Protecting groups are commonly used in organic synthesis to inhibit reactions at one functional group in a molecule while a different functional group is being transformed by a reagent that would react at both functional groups. Common protecting groups for alcohols include esters such as alkyl (e.g., C1-C4) or aryl carboxylate or sulfonate esters. For example, activation of alcohols by formation of toluene sulfonate esters is a common step carried out by reaction of the alcohol with toluene sulfonyl chloride in the presence of a base to react with the acid formed. Such activation allows alkylation by displacement of these activated alcohols (leaving groups) by anionic moieties or nucleophiles.

Alternatively, these alcohol functions can be replaced by halogens to result in alternative leaving groups that may prove more compatible for alkylation by some nucleophiles. Amines can be protected by formation of benzylamines or as the amide or sulfonamide.

Compound 9 is then converted to Compound 10. The resulting benzyl-protected amine can be removed or deprotected by catalytic hydrogenation. Amide and sulfonamide protecting groups can be removed by hydrolysis in aqueous acid. Acid groups, such as carboxyl or phosphoric, can be protected by formation of alkyl or aryl esters created by the reaction with an alkyl or aryl alcohol.

Compound 10 is then converted to form the isomeric compound of the present invention. For example, the resulting ester protecting groups of Compound 10 can be removed by hydrolysis with aqueous acid.

The following is a non-limiting synthetic scheme for the preparation of the substantially enantiomerically pure compound of the present invention:

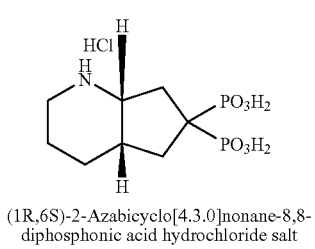

(1R,6S)-2-Azabicyclo[4.3.0]nonane-8,8-diphosphonic acid hydrochloride salt

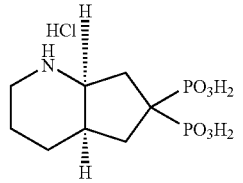

(1S,6R)-2-Azabicyclo[4.3.0]nonane-8,8-diphosphonic acid hydrochloride salt

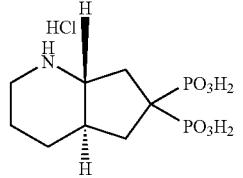

(1R,6R)-2-Azabicyclo[4.3.0]nonane-8,8-diphosphonic acid hydrochloride salt

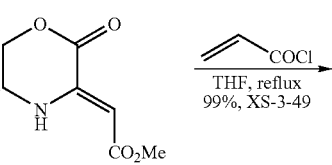

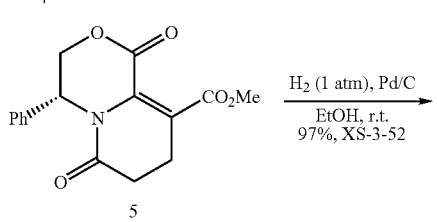

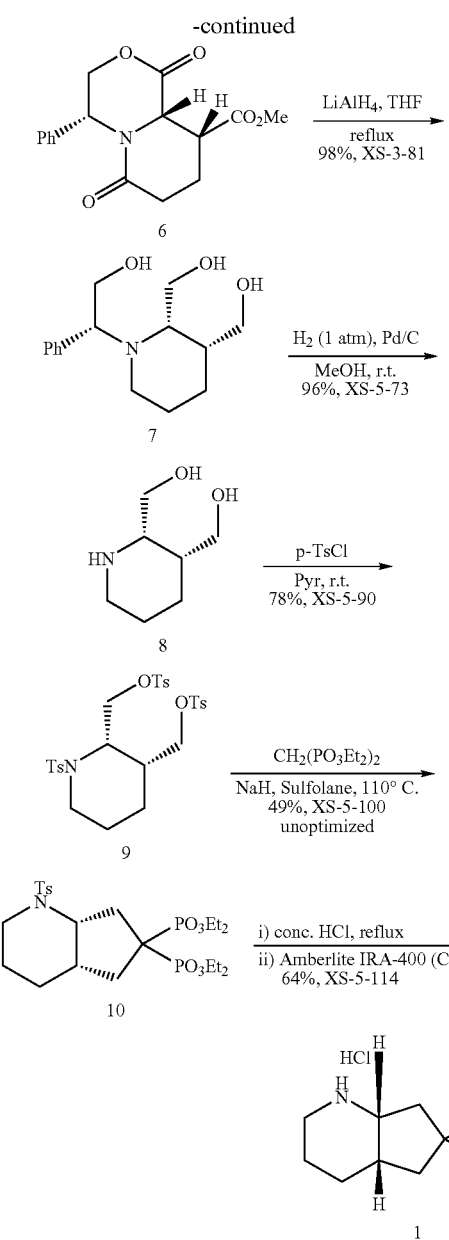

Note:

Compound 4 was made from (R)-2-Phenylglycinol following the procedure by Tamura, M.; Harada, K. *Bull. Chem. Soc. Jpn.* 1980, 53, 561-562.

Compound 6 was made following the preparation of ent-6 from the procedure by Agami, C.; Hamon, L.; Kadouri-Puchot, C.; Le Guen, V. *J. Org. Chem.* 1996, 61, 5736-42.

(R)-3-Methoxycarbonylmethylene-5-phenyl-3,4,5,6-tetrahydro-2H-1,4-oxazin-2-one (4) may be made according to the procedure by Tamura, M.; Harada, K. *Bull. Chem. Soc. Jpn.* 1980, 53, 561-562.

(4R)-1,6-Dioxo-4-phenyl-1,3,4,6,7,8-hexahydropyrido[2,1-c][1,4]oxazine-9-carboxylic acid methyl ester (5) and [4R-4a,9a,9aa]-1,6-Dioxo-4-phenyloctahydropyrido[2,1-c][1,4]oxazine-9-carboxylic acid methyl ester (6) may be made according to the procedure of the syntheses of ent-5 and ent-6 by Agami, C.; Hamon, L.; Kadouri-Puchot, C.; Le Guen, V. *J. Org. Chem.* 1996, 61, 573642.

N-(1R-Phenyl-2-hydroxyethyl)-2S,3R-bis(hydroxymethyl)piperidine (7)

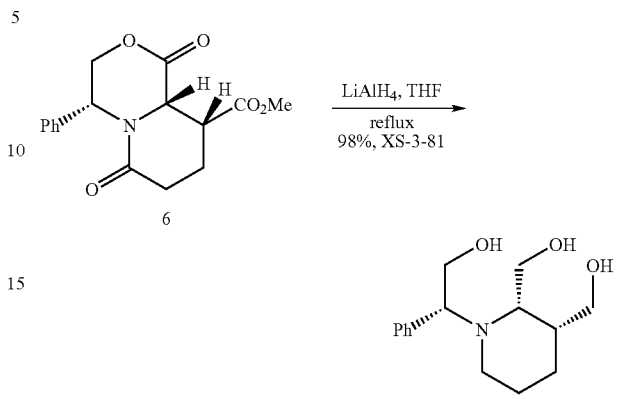

LiAlH$_4$ (1.86 g, 49 mmol) is added portionwise into a solution of 6 (2.12 g, 7.0 mmol) in THF (80 mL) at 0° C. The mixture is then heated to reflux for 22 h, cooled to 0° C. The reaction mixture is successively treated with H$_2$O (2 mL), 15% NaOH (2 mL) and H$_2$O (6 mL), stirred at room temperature for 1 h, filtered through Celite and concentrated in vacuo to provide 7 as a white solid (1.81 g, 98%). An analytical sample is obtained by recrystallization from CH$_2$Cl$_2$-CH$_3$OH.

$^1$H NMR (400 MHz, CD$_3$OD) δ7.40-7.38 (m, 2H), 7.34-7.30 (m, 2H), 7.28-7.25 (m, 1H), 4.07-4.06 (m, 1H), 3.93-3.83 (m, 2H), 3.76-3.72 (dd, J$_1$=6 Hz, J$_2$=5 Hz, 1H), 3.65-3.61 (dd, J$_1$=6 Hz, J$_2$=5 Hz, 1H), 3.49-3.42 (m, 2H), 3.23-3.21 (m, 1H), 2.70-2.68 (m, 2H), 2.07-2.04 (m, 1H), 1.55-1.53 (m, 1H), 1.37-1.34 (m, 3H)

$^{13}$C NMR (125 MHz, CD$_3$OD) δ128.0, 127.9, 126.9, 66.8, 63.6, 63.4, 59.5, 56.6, 41.6, 38.3, 23.5, 22.4

IR (film) 3331, 2928, 2360, 2340, 1452, 1028, 860, 765 cm$^{-1}$

HRMS Calcd for C$_{15}$H$_{24}$NO$_3$ (M$^+$+H): 266.1751, Found: 266.1745 (EI)

[α]$_D^{20}$ –36.9° (c 1, CH$_3$OH)

2S,3R-bis(hydroxymethyl)piperidine (8)

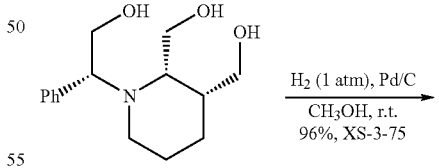

A suspension of 7 (0.53 g, 2.0 mmol) and 10% Pd/C (0.106 g, 5 mol %) in CH$_3$OH (25 ml) is stirred under 1 atm H$_2$ (balloon) at room temperature for 15 h, then filtered through Celite and concentrated in vacuo to provide a 1:1 mixture of 8 (about 96% yield) and 2-phenylethanol, which is used directly to the next step without purification. An analytical sample of 8 is obtained by chromatography of the crude residue on silica gel (100% CH$_3$OH).

$^1$H NMR (400 MHz, CDCl$_3$) δ4.08 (bs, 3H), 3.79-3.65 (m, 4H), 3.05-3.01 (m, 1H), 2.99-2.95 (m, 1H), 2.73-2.67 (m. 1H), 1.84-1.81 (m, 1H), 1.73-1.64 (m, 2H), 1.63-1.58 (m, 1H), 1.50-1.47 (m, 1H)

$^{13}$C NMR (125 MHz, CDCl$_3$) δ63.4, 62.5, 59.1, 45.1, 37.4, 28.2, 23.2

IR (film) 3302, 2930, 2360, 2340, 1633, 1443, 1037, 732cm$^{-1}$

HRMS Calcd for C$_7$H$_{15}$NNaO$_2$ (M$^+$+Na): 168.0995, Found: 168.0993 (EI)

N-(p-Toluenesulfonyl)-(2S,3R)-piperidine-2,3-dimethyl bis-p-toluenesulfonate (9)

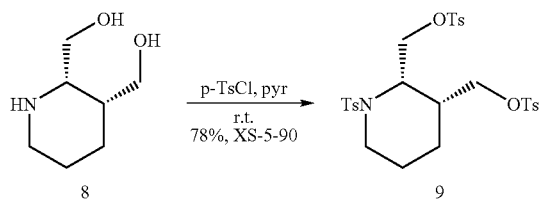

p-TsCl (2.99 g, 15.7 mmol) is added portionwise over 30 min into a solution of 1:1 mixture of 8 (2.62 mmol) and 2-phenylethanol in pyridine (2.6 mL) at 0° C. The mixture is allowed to stir at room temperature for 13 h, then poured into ice-water (10 mL). The aqueous layer is extracted with CH$_2$Cl$_2$ (3×20 mL) and the combined organic solutions are dried over MgSO$_4$ and concentrated in vacuo to give a brown oil, which is chromatographed on silica gel (elution by 100% CH$_2$Cl$_2$) to provide 9 as a colorless oil (1.24 g, 78%).

$^1$H NMR (400 MHz, CDCl$_3$) δ7.77-7.75 (m, 2H), 7.71-7.66 (m, 4H), 7.39-7.34 (m, 4H), 7.28-7.26 (m, 2H), 4.36-4.32 (m, 1H), 4.12-4.08 (m, 1H), 4.01-3.97 (m, 1H), 3.86-3.83 (m, 2H), 3.70-3.66 (d, J=17 Hz, 1H), 2.87-2.80 (t, J=12 Hz, 1H), 2.47 (s, 3H), 2.46 (s, 3H), 2.42 (s, 3H), 2.04-2.01 (m, 1H), 1.58-1.53 (m, 2H), 1.31-1.27 (m, 2H)

$^{13}$C NMR (125 MHz, CDCl$_3$) δ145.3, 143.5, 137.6, 132.3, 132.0, 130.1, 130.0, 129.8, 128.0, 127.9, 127.0, 70.3, 66.6, 51.6, 41.2, 37.7, 29.7, 23.8, 22.2, 21.7, 21.5

IR (film) 2927, 2360, 1597, 1494, 1452, 1361, 1176, 962, 815, 665 cm$^{-1}$

HRMS Calcd for C$_{28}$H$_{33}$NNaO$_8$S$_3$ (M$^+$+Na): 630.1260, Found: 630.1264 (EI)

Tetraethyl 2-p-toluenesulfonyl-(1R,6S)-2-azabicyclo[4.3.0]nonane-8,8-diphosphonate (10)

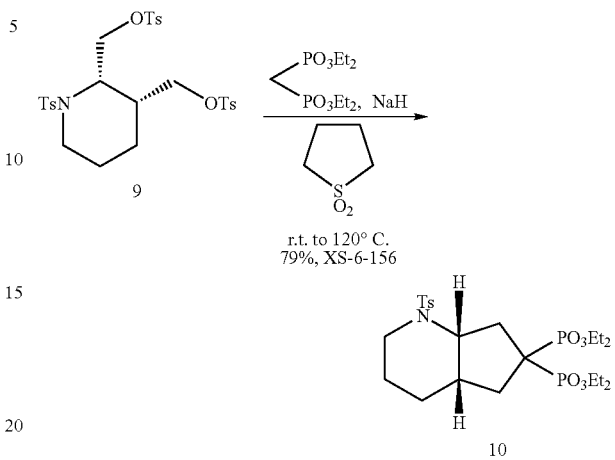

A 10.53 g sample of CH$_2$(PO$_3$Et$_2$)$_2$ (36.5 mmol) is added dropwise to a suspension of NaH (0.838 g, 95% assay, 34.9 mmol) in sulfolane (15 mL) and the resulting mixture is stirred at room temperature for 50 min. A solution of 9 (9.65 g, 15.9 mmol) in sulfolane (17 mL) is added at room temperature over 1 h and the mixture is allowed to stir at 120° C. for 19 h, then cooled to room temperature. The reaction is quenched by H$_2$O (150 mL) and the aqueous layer is extracted with CH$_2$Cl$_2$ (3×150 mL). The combined organic solutions are dried over MgSO$_4$ and concentrated in vacuo to give a brown oil, that is heated under vacuum (250° C./1 mmHg) to remove the excess CH$_2$(PO$_3$Et$_2$)$_2$ and sulfolane. The residue is dissolved in Et$_2$O (150 mL) and washed with H$_2$O (4×6 mL), dried over MgSO$_4$ and concentrated in vacuo to an orange oil that is chromatographed on silica gel (0~5% ethanol in CH$_2$Cl$_2$) to provide 10 as a pale yellow oil (6.90 g, 79%).

$^1$H NMR (400 MHz, CDCl$_3$) δ7.66-7.64 (m, 2H), 7.26-7.24 (m, 2H), 4.62-4.59 (m, 1H), 4.20-4.05 (m, 8H), 3.74-3.70 (d, J=12 Hz, 1H), 2.81-2.80 (t, J=12 Hz, 1H), 2.41 (s, 3H), 2.40-2.38 (m, 1H), 2.23-2.00 (m, 2H), 1.98-1.91 (m, 3H), 1.68-1.64 (m, 1H), 1.53-1.50 (m, 1H), 1.46-1.45 (m, 1H), 1.36-1.22 (m, 12H)

$^{13}$C NMR (125 MHz, CDCl$_3$) δ143.0, 137.7, 129.6, 127.0, 62.9 (d, J$_{C-P}$=9 Hz), 62.8 (d, J$_{C-P}$=9 Hz), 62.4 (d, J$_{C-P}$=8 Hz), 62.3 (d, J$_{C-P}$=8 Hz), 55.3 (d, J$_{C-P}$=14 Hz), 42.3 (t, J$_{C-P}$=171 Hz), 40.4, 35.6, 33.1, 29.0, 25.6, 24.1, 21.4, 16.5 (d, J$_{C-P}$=3 Hz)

IR (film) 3476, 2982, 2934, 1647, 1598, 1445, 1336, 1246, 1158, 1042,972 cm$^{-1}$ HRMS Calcd for C$_{23}$H$_{39}$NNaO$_8$P$_2$S (M$^+$+Na): 574.1764, Found: 574.1762 (EI)

(1R,6S)-2-Azabicyclo[4.3.0]nonane-8,8-diphosphonic acid hydrochloride salt (1)

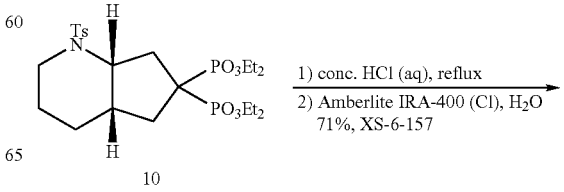

-continued

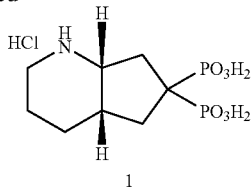

A solution of 10 (6.50 g, 11.8 mmol) in conc. HCl (100 mL) is heated to reflux for 18 h. The mixture is cooled to room temperature, washed with EtOAc (2×20 mL) and the aqueous solution is concentrated in vacuo to a brown residue (10 mL). The crude material is loaded on a Amberlite IRA-400 (Cl) resin column (150 mL), wherein the column is preeluted with 6 M HCl (600 mL) and rinsed with $H_2O$ (1 L) to pH 6~7. The column is eluted with water (3 L) and concentrated in vacuo to give a brown solid, which is dissolved in 6 M HCl (40 mL) and added with activated carbon (1.5 g) and heated to reflux for 5 min, cooled to 50° C., filtered through Celite and the filtrate is concentrated in vacuo to give 1 as a pale yellow solid (2.68 g 71%).

$^1$H NMR (400 MHz, $D_2O$) δ3.55 (br s, 1H), 3.24 (br s, 1H), 2.75 (br s, 1H), 2.46 (br s, 2H), 2.21 (br s, 3H), 1.71 (br s, 3H), 1.63 (br s, 1H)

$^{13}$C NMR (125 MHz, $D_2O$) δ58.7, 43.0, 37.0, 35.5, 31.6, 30.1, 21.2, 16.3

LRMS Calcd for $C_8H_{16}NO_6P_2$ (M$^-$–HCl–H): 284.0, Found: 284.1 (Lcq, Neg)

Anal. Calcd for $C_8H_{18}ClNO_6P_2$: C, 29.87, H, 5.64, N, 4.35. Found: C, 30.79, H, 5.98, N, 4.31.

m.p. >250° C.

Pharmaceutical Compositions

The present invention further relates to a pharmaceutical composition comprising the substantially enantiomerically pure isomer herein.

The composition further comprises a pharmaceutically-acceptable excipient. The term "pharmaceutically-acceptable excipient," as used herein, means any physiologically inert, pharmacologically inactive material known to one skilled in the art, which is compatible with the physical and chemical characteristics of the isomer herein. Pharmaceutically-acceptable excipients include, but are not limited to, polymers, resins, plasticizers, fillers, lubricants, diluents, binders, disintegrants, solvents, co-solvents, surfactants, preservatives, sweetening agents, flavoring agents, pharmaceutical grade dyes or pigments, and viscosity agents.

The compositions herein may be oral dosage forms, or any other form that is suitable for its intended use. Typical oral dosage forms may include tablets or capsules. In one embodiment, the composition is a tablet.

In one embodiment, the compositions herein comprise from about 0.001 mg to about 1 gram, or from about 0.01 mg to about 0.5 gram, or from about 0.1 mg to about 0.3 gram, or from about 1 mg to about 0.1 gram of the substantially enantiomerically pure isomer herein.

Flavoring agents and dyes and pigments among those useful herein include those described in *Handbook of Pharmaceutical Excipients* (4th ed., Pharmaceutical Press 2003).

Suitable co-solvents include, but are not limited to, ethanol, isopropanol, and acetone.

Suitable surfactants include, but are not limited to, polyoxyethylene sorbitan fatty acid esters, polyoxyethylene monoalkyl ethers, sucrose monoesters, sodium lauryl sulfate, Tween 80®, and lanolin esters and ethers.

Suitable preservatives include, but are not limited to, phenol, alkyl esters of parahydroxybenzoic acid, benzoic acid and the salts thereof, boric acid and the salts thereof, sorbic acid and the salts thereof, chlorbutanol, benzyl alcohol, thimerosal, phenylmercuric acetate and nitrate, nitromersol, benzalkonium chloride, cetylpyridinium chloride, methyl paraben, and propyl paraben.

Suitable fillers include, but are not limited to, starch, lactose, sucrose, maltodextrin, and microcrystalline cellulose.

Suitable plasticizers include, but are not limited to, triethyl citrate, polyethylene glycol, propylene glycol, dibutyl phthalate, castor oil, acetylated monoglycerides, and triacetin.

Suitable polymers include, but are not limited to, ethylcellulose, cellulose acetate trimellitate, hydroxypropylmethylcellulose phthalate, cellulose acetate phthalate, polyvinyl acetate phthalate, and Eudragit® L 30-D, Eudragit® L 100-55, and Eudragit® S 100 (Röhm Pharma GmbH and Co. KG, Darmstadt, Germany), and Acryl-EZE® and Sureteric® (Colorcon, Inc., West Point, Pa.).

Suitable lubricants include, but are not limited to, magnesium stearate, stearic acid, and talc.

The pharmaceutical compositions of the present invention may optionally comprise a chelating agent. The term "chelating agent," as used herein, means a molecule containing two or more electron donor atoms that can form coordinate bonds to a single metal ion. The term "chelating agent" is understood to include the chelating agent as well as salts thereof. For example, the term "chelating agent" includes citric acid as well as its salt forms. The most common and widely used chelating agents coordinate to metal atoms through oxygen or nitrogen donor atoms, or both. Other less common chelating agents coordinate through sulfur in the form of —SH (thiol or mercapto) groups. After the first coordinate bond is formed, each successive donor atom that binds creates a ring containing the metal atom. A chelating agent may be bidentate, tridentate, tetradentate, etc., depending upon whether it contains two, three, four, or more donor atoms capable of binding to the metal atom. See Kirk-Othmer Encyclopedia of Chemical Technology (4th ed. 2001).

Chelating agents suitable for use in the present invention include any pharmaceutically-acceptable chelating agent. Non-limiting examples of chelating agents suitable for use in the present invention include EDTA, citric acid, malic acid, tartaric acid, lactic acid, aspartic acid, glutamic acid, lysine, sodium hexametaphosphate, and combinations thereof. In one embodiment of the present invention, the chelating agent is EDTA, citric acid, or sodium hexametaphosphate.

In another embodiment of the invention, a monodentate complexing agent may be used in place of a polydentate chelating agent. Suitable monodentate complexing agents include, but are not limited to, phosphates (e.g., sodium phosphate, sodium aluminum phosphate, sodium acid phosphate, dipotassium phosphate, disodium phosphate, monobasic) and carboxylic acids (e.g., fumaric acid, acetic acid). A preferred monodentate complexing agent is acetic acid.

The amount of chelating agent present in the oral dosage form of the present invention will depend on the particular chelating agent selected and the amount of bisphosphonate active ingredient present in the oral dosage form. Generally, the oral dosage forms of the present invention will contain a safe and effective amount of a chelating agent suitable for achieving the desired chelating effect. In one embodiment, the oral dosage form contains from about 10 mg to about 1000 mg of a chelating agent per unit dose. In another embodiment, the oral dosage forms contain from about 10 mg to about 500 mg of a chelating agent per unit dose. When the chelating agent is EDTA, the preferred range is from about 10 mg to about 500 mg, preferably from about 25 mg to about 250 mg per unit dose. When the chelating agent is citric acid or any other chelating agent, the preferred range is from about 25 mg to about 1000 mg, preferably from about 50 mg to about 500 mg per unit dose.

The pharmaceutical compositions of the present invention may optionally comprise a film coating or an enteric coating. Excipients suitable for use in a film coating include, but are not limited to, hydroxypropylmethylcellulose, hydroxypropylcellulose, gelatin, polyvinylpyrrolidone, lactose, polyethylene glycol, talc, microcrystalline cellulose, and polyvinyl alcohol. Excipients suitable for use in an enteric coating include, but are not limited to, cellulose acetate trimellitate, hydroxypropylmethylcellulose phthalate, cellulose acetate phthalate, polyvinyl acetate phthalate, Eudragit® L 30-D, Eudragit® L 100-55, Eudragit® S 100 (Röhm Pharma GmbH and Co. KG, Darmstadt, Germany), Acryl-EZE® and Sureteric® (Colorcon, Inc., West Point, Pa.), triethyl citrate, polyethylene glycol, propylene glycol, dibutyl phthalate, castor oil, acetylated monoglycerides, triacetin, and talc.

Method of Use

The present invention further relates to a method of treating or preventing a condition of bone metabolism comprising administering to a human or other mammal in need thereof a safe and effective amount of a -pharmaceutical composition delivered to said human or other mammal, wherein the composition comprises the substantially enatiomerically pure compound herein.

Conditions characterized by abnormal calcium and phosphate metabolism include, but are not limited to, osteoporosis, Paget's Disease (osteitis deformans), hyperparathyroidism, hypercalcemia of malignancy, osteolytic bone metastasis, myositis ossificans progressiva, calcinosis universalis, arthritis, neuritis, bursitis, tendonitis, and other inflammatory conditions which predispose involved tissue to deposition of calcium phosphates.

The oral dosage forms of the present invention are suitable for administration to a patient according to a continuous dosing interval of daily, weekly, three times per month, twice monthly, and monthly.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A pharmaceutical composition comprising (1R,6S)-2-azabicyclo-[4.3.0]nonane-8,8-diphosphonic acid, or a salt thereof, wherein the pharmaceutical composition is substantially free of (1S6R)-2-azabicyclo-[4.3.0]nonane-8,8-diphosphonic acid, and wherein the pharmaceutical composition is characterized by having an enhanced inhibitory effect on farnesyl pyrophosphate synthase compared to the inhibitory effect of racemic 2-azabicyclo-[4.3.0]nonane-8,8-diphosphonic acid or (1S,6R)-2-azabicyclo-[4.3.0]nonane-8,8-diphosphonic acid substantially free of(1R,6S)-2-azabicyclo-[4.3.0]nonane-8,8-diphosphonic acid.

2. The pharmaceutical composition according to claim 1, wherein the (1R,6S)-2-azabicyclo-[4.3.0]nonane-8,8-diphosphonic acid, or a salt thereof, is free of (1S,6R)-2-azabicyclo-[4.3.0]nonane-8,8-diphosphonic acid.

3. The pharmaceutical composition according to claim 1 further comprising a pharmaceutically acceptable excipient.

4. The pharmaceutical composition according to claim 3, wherein the pharmaceutical composition comprises a therapeutically effective amount of the (1R,6S)-2-azabicyclo-[4.3.0]nonane-8,8-diphosphonic acid, or a salt thereof.

5. The pharmaceutical composition according to claim 4, wherein the therapeutically effective amount of the (1R,6S)-2-azabicyclo-[4.3.0]nonane-8,8-diphosphonic acid, or a salt thereof, is effective in modulating calcium metabolism in a recipient animal or human recipient.

6. The pharmaceutical composition according to claim 1, wherein the (1R,6S)-2-azabicyclo-[4.3.0]nonane-8,8-diphosphonic acid, or a salt thereof, that is substantially free of (1S,6R)-2-azabicyclo-[4.3.0]nonane-8,8-diphosphonic acid is prepared by a method comprising the steps of:

(a) conversion of [4R-4α,9α,9aα]-1,6-Dioxo-4-phenyloctahydropyrido[2,1-c][1,4]oxazine-9-carboxylic acid methyl ester (Compound 6) having the formula:

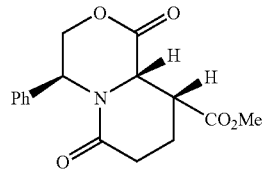

to form N-(1R-Phenyl-2-hydroxyethyl)-2S,3R -bis (hydroxymethyl)piperidine (Compound 7) having the formula:

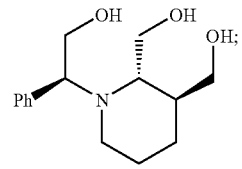

(b) conversion of N-(1R-Phenyl-2-hydroxyethyl)-2S,3R-bis(hydroxymethyl)piperidine (Compound 7) having the formula:

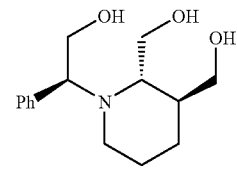

to form 2S,3R-bis(hydroxymethyl)piperidine (Compound 8) having the formula:

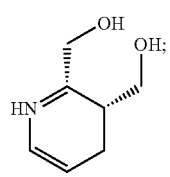

(c) conversion of 2S,3R-bis(hydroxymethyl)piperidine (Compound 8) having the formula:

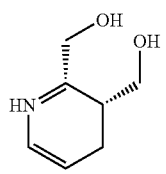

to form N-(p-Toluenesulfony1)-(2S,3R)-piperidine-2,3-dimethyl bis-p-toluenesulfonate (Compound 9) having the formula:

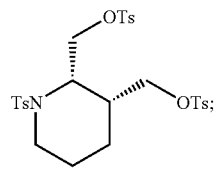

(d) conversion of N-(p-Toluenesulfony1)-(2S,3R)-piperidine-2,3-dimethyl bis-p-toluenesulfonate (Compound 9) having the formula:

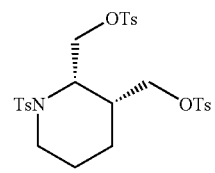

to form Tetraethyl 2-p-toluenesulfonyl-(1R,6S)-2azabicyclo[4.3.0]nonane-8,8-diphosphonate (Compound 10) having the formula:

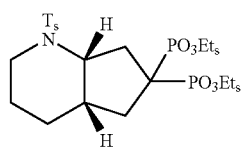

and (e) conversion of Tetraethyl 2-p-toluenesulfonyl-(1R,6S)-2azabicyclo[4.3.0]nonane-8,8-diphosphonate (Compound 10) having the formula:

to form (1R,6S)-2-azabicyclo-[4.3.0]nonane-8,8-diphosphonic acid having the formula:

or a salt thereof, that is substantially free of (1S,6R)-2-azabicyclo-[4.3.0]nonane-8,8-diphosphonic acid.

* * * * *

UNITED STATES PATENT AND TRADEMARK OFFICE
CERTIFICATE OF CORRECTION

| | | |
|---|---|---|
| PATENT NO. | : 7,781,418 B2 | |
| APPLICATION NO. | : 12/001318 | |
| DATED | : August 24, 2010 | |
| INVENTOR(S) | : Ebetino et al. | |

It is certified that error appears in the above-identified patent and that said Letters Patent is hereby corrected as shown below:

Title page item (73) should be

Isis Innovation Ltd., Summertown, Oxford (GB)
The University of Rochester, Rochester, New York (US)

Signed and Sealed this
Twenty-fifth Day of January, 2011

David J. Kappos
*Director of the United States Patent and Trademark Office*